United States Patent [19]

Hanawa et al.

[11] Patent Number: 5,512,422

[45] Date of Patent: Apr. 30, 1996

[54] METHOD OF FORMING RESIST PATTERN AND ORGANIC SILANE COMPOUND FOR FORMING ANTI-REFLECTION FILM FOR USE IN SUCH METHOD

[75] Inventors: Tetsuro Hanawa; Maria O. de Beeck, both of Hyogo, Japan

[73] Assignee: Mitsubishi Denki Kabushiki Kaisha, Tokyo, Japan

[21] Appl. No.: 205,480

[22] Filed: Mar. 4, 1994

Related U.S. Application Data

[62] Division of Ser. No. 814,632, Dec. 30, 1991, Pat. No. 5,380,889.

[30] Foreign Application Priority Data

Aug. 8, 1991 [JP] Japan ................... 3-199603

[51] Int. Cl.$^6$ ................... G03C 5/00
[52] U.S. Cl. ................... 430/325; 430/272.1; 430/273.1; 430/313; 430/510; 430/945; 522/75
[58] Field of Search ................... 430/272, 313, 430/325, 273, 510; 522/75

[56] References Cited

U.S. PATENT DOCUMENTS

| | | | |
|---|---|---|---|
| 4,362,809 | 12/1982 | Chen et al. | 430/312 |
| 4,587,203 | 5/1986 | Brault et al. | 430/272 |
| 4,623,739 | 11/1986 | Watanabe et al. | 556/410 |
| 4,981,986 | 1/1991 | Yoshioka et al. | 556/410 |
| 4,985,333 | 1/1991 | Tokutake et al. | 430/192 |
| 5,118,582 | 6/1992 | Veno et al. | 430/270 |
| 5,118,724 | 6/1992 | Frances et al. | 522/99 |
| 5,162,559 | 11/1992 | Wilharm et al. | 556/411 |

FOREIGN PATENT DOCUMENTS

| | | |
|---|---|---|
| 3036710 | 5/1982 | Germany . |
| 3627757 | 2/1988 | Germany . |
| 3842896 | 11/1989 | Germany . |

OTHER PUBLICATIONS

Lamola et al, Chemically Amplified Resists, Solid State Technology; Aug. 1991 pp. 53–60.

*Primary Examiner*—Marion E. McCamish
*Assistant Examiner*—Bernard P. Codd
*Attorney, Agent, or Firm*—Lowe, Price, LeBlanc & Becker

[57] ABSTRACT

Methods of forming a resist pattern allow the size of the resist pattern to be controlled in its formation, and the size of the underlying substrate to be controlled in etching the same even with a step portion existing on the substrate. The methods of forming a resist pattern on a substrate by lithography use far-ultra violet light. An organic silane compound for forming an anti reflection film on the surface of a substrate includes a silicon atom, a leaving group bound to the silicon atom and replaceable with an hydroxyl group existing in the surface of the semiconductor substrate to bind covalently the semiconductor substrate and the organic silane compound, and a substituent group absorbing the far-ultra violet light. The substrate is coated with the organic silane compound. Resist is applied onto the substrate coated with the organic silane compound. The resist is exposed selectively using far-ultra violet light, and then developed.

10 Claims, 10 Drawing Sheets

R1, R2, R3, R4: HYDROGEN OR ALKYL GROUP

FIG. 2(b)

R1, R2, R3, R4, R5, R6: HYDROGEN OR ALKYL GROUP

R: HYDROGEN ATOM OR ALKYL GROUP

METHOD OF FORMING RESIST PATTERN AND ORGANIC SILANE COMPOUND FOR FORMING ANTI-REFLECTION FILM FOR USE IN SUCH METHOD

This application is a division of application Ser. No. 07/814,632, filed Dec. 30, 1991, U.S. Pat. No. 5,380,889.

BACKGROUND OF THE INVENTION

FIELD OF THE INVENTION

The present invention relates generally to a method of forming a resist pattern, and more specifically, to a method of forming a resist pattern on a semiconductor substrate by means of lithography using far-ultra violet light. The present invention further relates to an organic silane compound for forming an anti-reflection film used in such a method of forming a resist pattern.

Today, in the process of manufacturing 64M Dynamic Random Access Memory devices, development of "quarter micron lithography technology" is in demand. Recently, lithography using far-ultra violet light such as excimer laser light utilizes a resist of the chemical amplification negative type. The resist is formed of a base resin which absorbs little far-ultra violet ray an acid producing agent which is decomposed by photochemical reaction and produces acid and a cross linking agent for cross linking the base resin by acid catalyzed reaction.

Figure 6A:
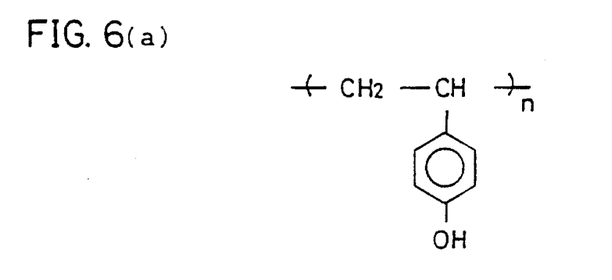
FIGS. 6(a)–(c) are is a representation showing the main components of resist of chemical amplification negative type used in a conventional method or in the present invention by way of chemical structural formula.
Figure 6B:
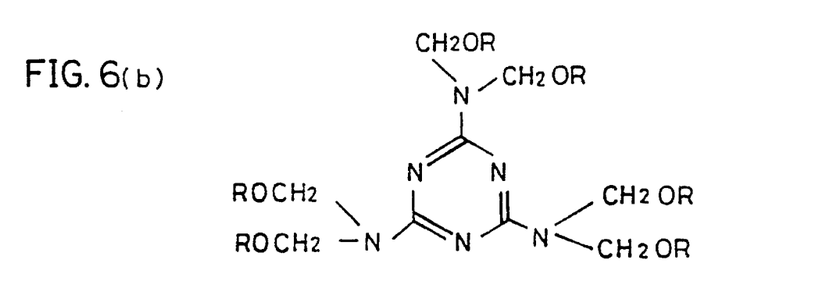
Figure 6C:
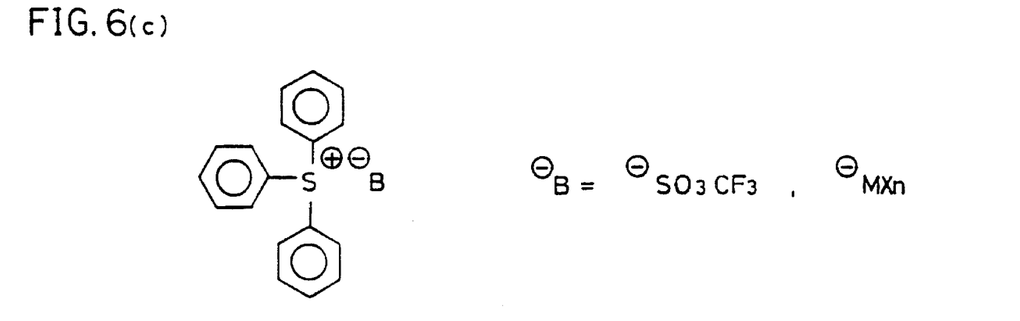

FIG. 6 is a representation showing the chemical structural formula of components contained in a resist of the chemical amplification negative type. The resist of the chemical amplification negative type is formed of a base resin of poly-p-hydroxystyrene as shown in FIG. 6 (a), a cross linking agent of melamine type having at least two cross linking points as shown in FIG. 6 (b), and an acid producing agent as shown in FIG. 6 (c). In the figures, n is a natural number representing a degree of polymerization, R represents an alkyl group, M represents a metal element such as arsenic and antimony, and X represents a halogen element.

FIG. 7 is a partially sectional view showing a semiconductor device in the steps in the order of a conventional method of pattern formation.

Referring to FIG. 7 (a), a contact reinforcing layer 9 is formed on a semiconductor substrate 2 for reinforcing the close contact between semiconductor substrate 2 and a resist layer of chemical amplification negative type subsequently to be applied thereon. Contact reinforcing layer 9 is obtained by applying hexamethyl disilazane onto semiconductor substrate 2, and by hard-baking the same.

Resist layer of chemical amplification negative type 3 having a thickness of 1.0 to 1.5 μm, the components of which are shown in FIG. 6, is formed on contact reinforcing layer 9. Resist layer of chemical amplification negative type 3 is formed by spin-coating the surface of semiconductor substrate 2 with resist solution and by soft-baking the same at a temperature around the range from 90° C. to 130° C.

Figure 8:
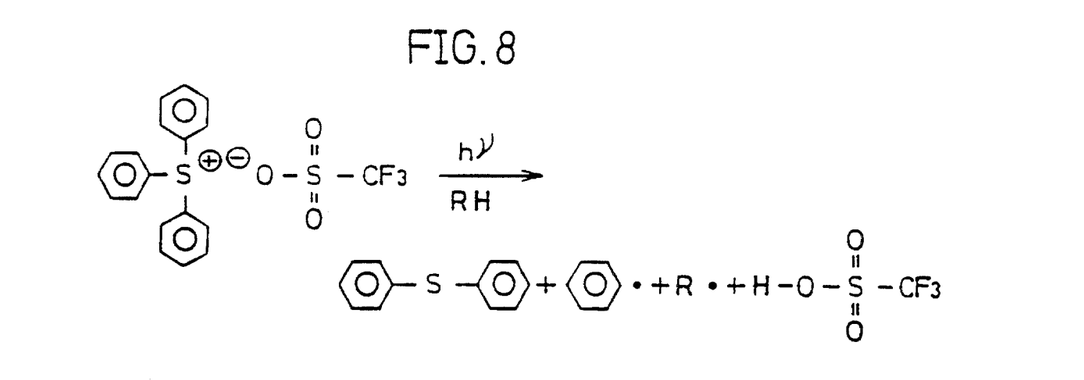
FIG. 8 is a representation showing the state of photo decomposition of acid producing agent contained in resist of chemical amplification negative type by way of reaction formula.

Referring to FIG. 7 (b), excimer laser light 7 is selectively irradiated upon a resist layer of the chemical amplification negative type 3 through a reticle 8. The selective irradiation of excimer laser light 7 allows an agent for generating acid, triphenyl-sulfonium-triflate, to decompose and generate trifluoromethanesulfonic acid and protons 4 in the exposed part 5 of resist layer of chemical amplification negative type 3, as indicated by the reaction formula in FIG. 8.

Referring to FIG. 7 (c), baking after the exposure is conducted for about a few minutes at a temperature around the range from 110° to 140° C. Description will be given on the state of cross linking in the exposed part of the base resin.

Figure 9:
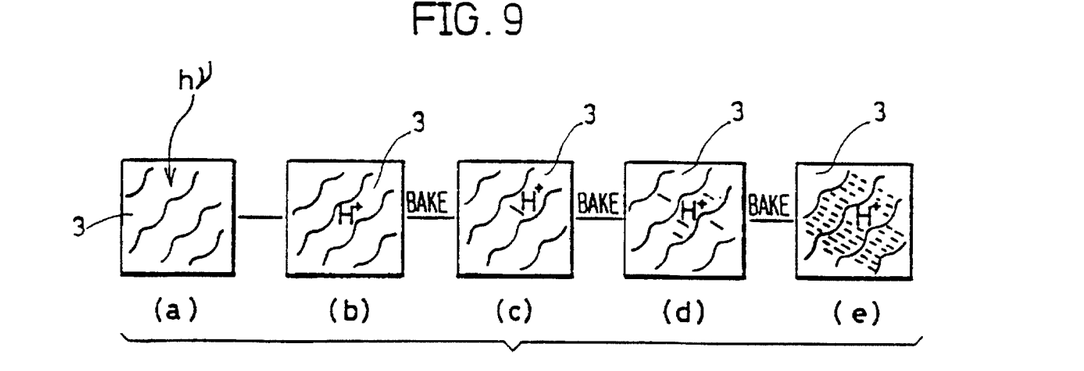
FIG. 9 is a representation showing the state of cross-linking in the exposed part of resist of chemical amplification negative type.
Figure 10A:
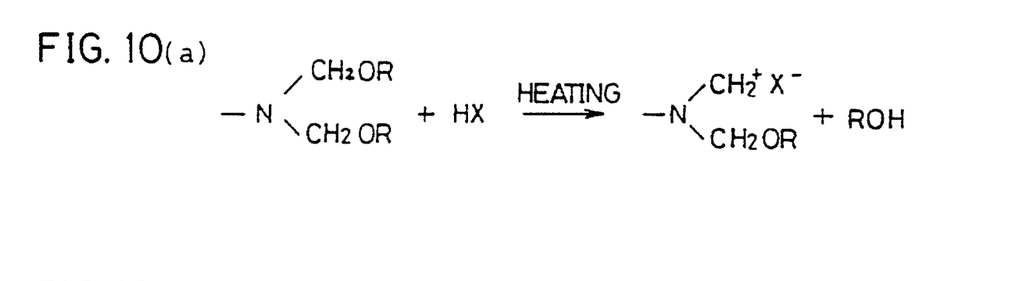
FIGS. 10(a)–(c) are is a representation showing the state of cross linking in the exposed part of resist of chemical amplification negative by way of reaction formula
Figure 10B:
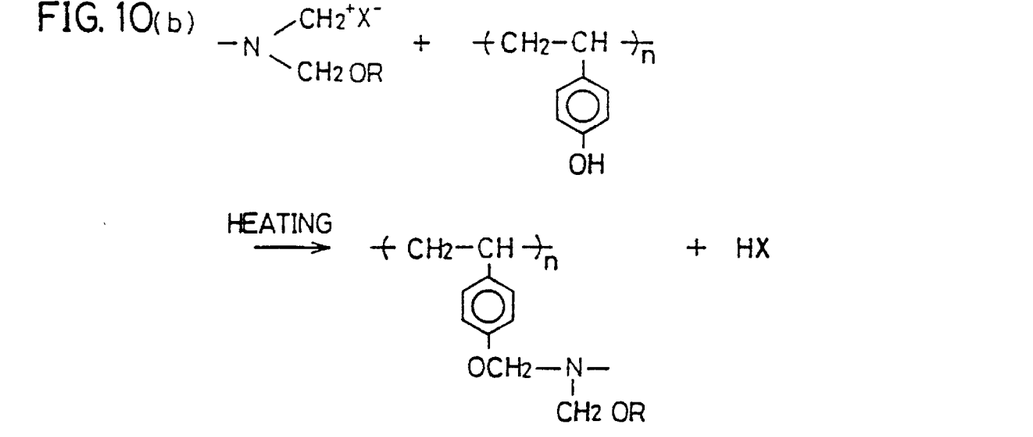
Figure 10C:
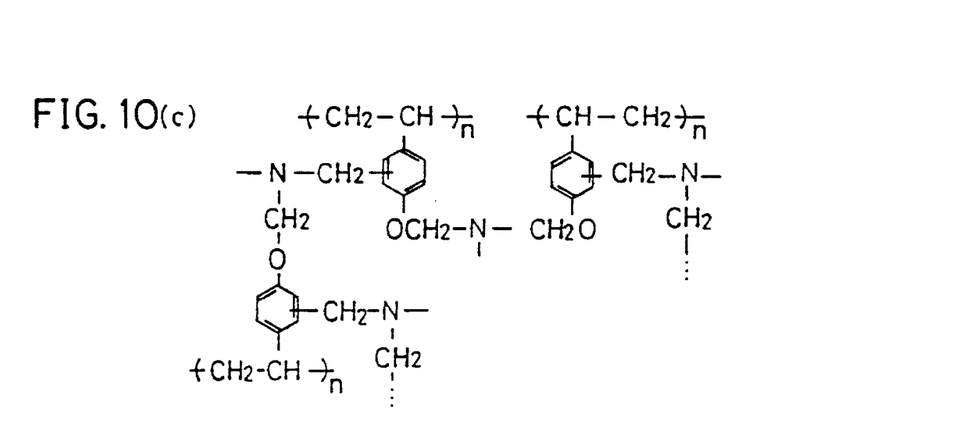

FIG. 9 (a) shows how excimer laser light irradiates resist 3. When the excimer laser light irradiates resist 3, referring to FIG. 9 (b), triphenyl-sulfonium-triflate decomposes to generate acid (H$^+$). Referring to FIG. 9 (c), baking of the resist causes one chain of the base resin to be cross linked in the presence of catalyst acid (H$^+$), and acid (H$^+$) is formed as a by-product. Referring to FIG. 9 (d), in the presence of the acid (H$^+$) as catalyst formed as the by-product, base resins are cross-coupled one after another in a chain reaction. Referring to FIG. 9 (e), the above-stated chain reaction produces a network of crosslinked base resins. The cross linking reaction is represented by the reaction formula shown in FIG. 10. In the reaction formula, HX represents acid (H$^+$). The crosslinked part becomes insoluble in a developing agent.

Figure 7A:
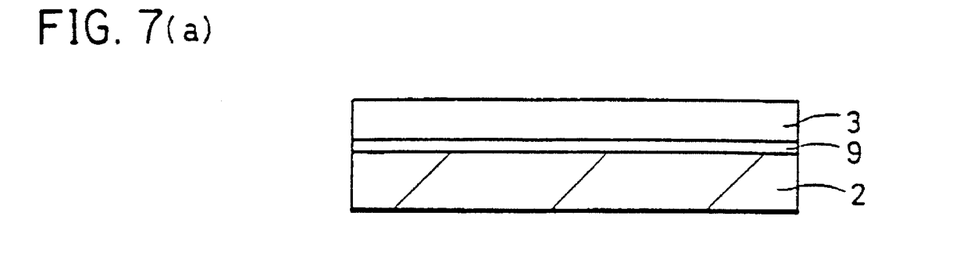
FIGS. 7(a)–(d) are is a partially sectional view showing a semiconductor device in the steps of a conventional manufacturing method in their order, using resist of chemical amplification negative type.
Figure 7B:
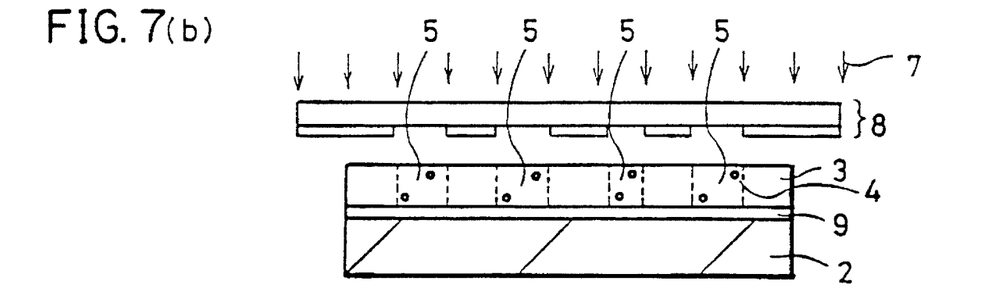
Figure 7C:
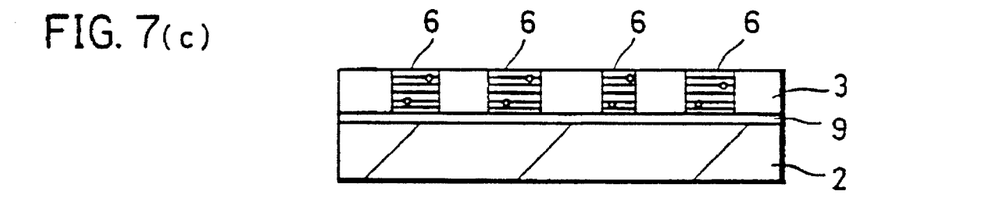
Figure 7D:
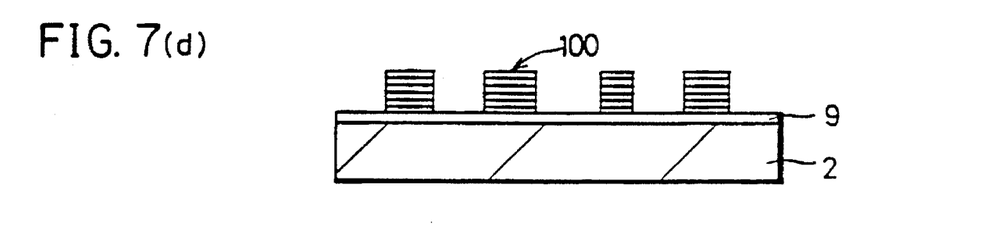

Referring back to FIG. 7 (c), the cross-linked part 6 of the resist becomes insoluble in a developing agent. Referring to FIG. 7 (d), when resist film 3 is developed with an alkaline developing agent of a suitable concentration, the non-exposed part (the part not crosslinked) dissolves by the developing agent, and a resist pattern is formed on semiconductor substrate 2. Then, semiconductor substrate 2 is etched, using the resist pattern 100 as a mask.

According to a conventional method of forming a resist pattern as described above, a very small good resist pattern having a rectangular cross section is produced with high sensitivity on a flat silicon substrate.

Figure 11:
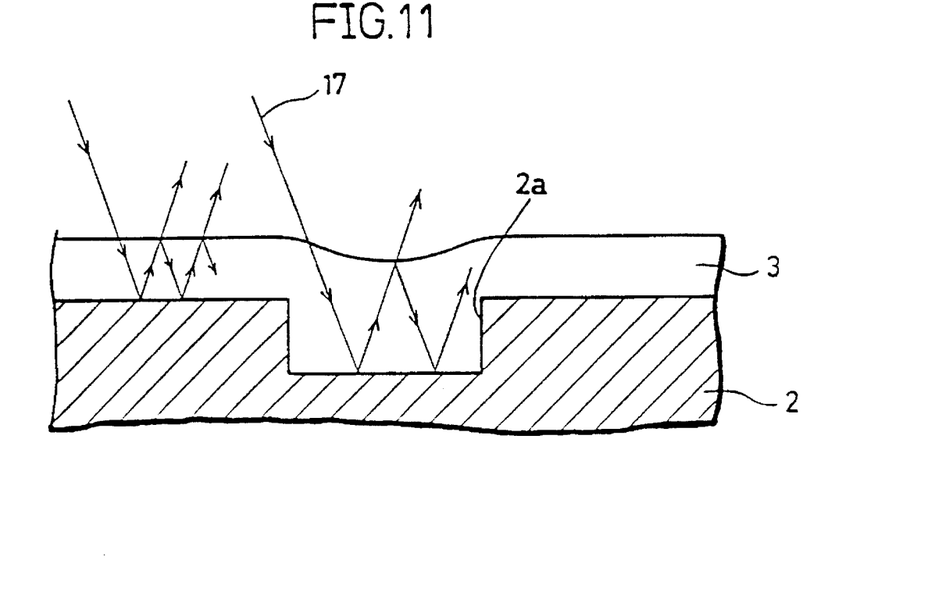
FIG. 11 is a representation for illustrating the effect of intra film multiple reflection effect.
Figure 12:
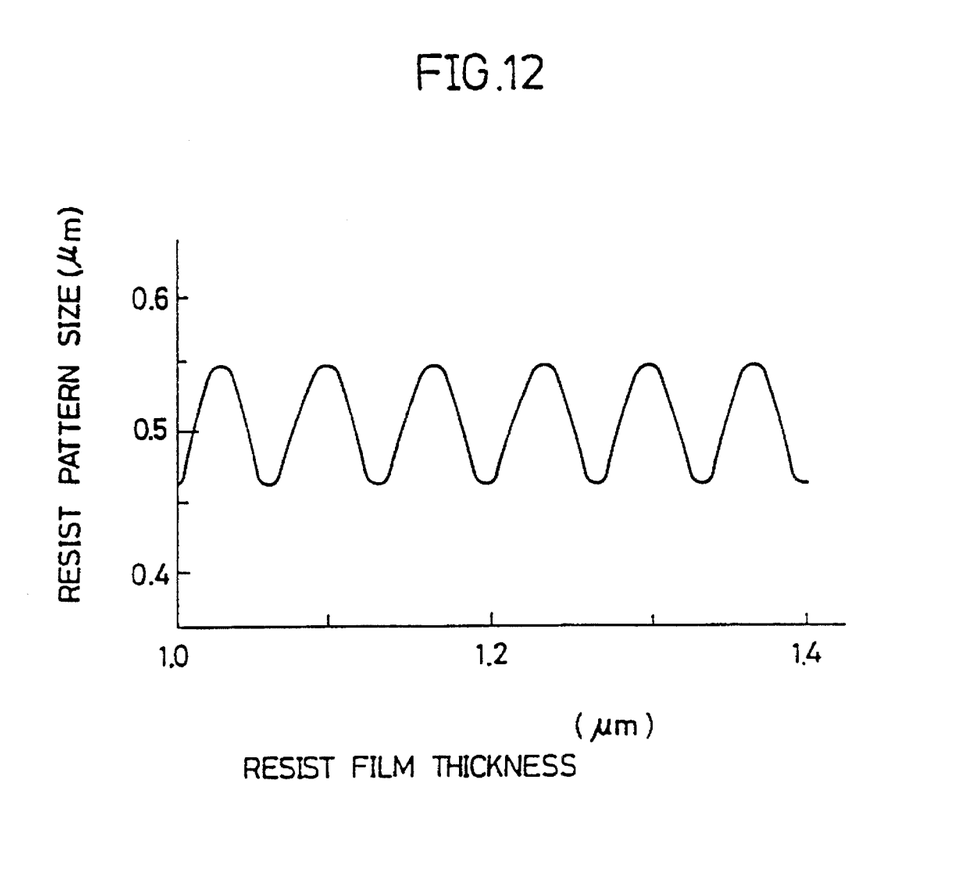
FIG. 12 is the thickness dependence of the dimension of resist pattern in resist when the effect of intra film multiple reflection effect is remarkable.

However, the base resin, poly-p-hydroxystyrene has high transmittance to excimer laser light and is therefore highly susceptible to intra film multiple reflection effect due to the excimer laser light 7 reflected from the underlying semiconductor substrate 2. As shown in FIG. 11, the intra film multiple reflection effect is caused by the coherence between the irradiated light 17 and the light reflected from the underlying semiconductor substrate 2. Referring to FIG. 12, a change in the thickness of the resist due to this intra film multiple reflection effect results in a great change in the size of a resultant resist pattern. Referring to FIG. 11, a step portion 2a existing in semiconductor substrate 2 causes a change in the thickness of resist 3, and the size of the resist pattern is not constant as a result.

A possible approach to prevent this intra film multi reflection effect uses an organic antireflection film. An organic antireflection film is formed by applying resist of novolak-naphthoquinonediazide type onto a semiconductor substrate, prior to application of the chemical amplification negative type resist and then by hard-baking the same. This method however bears the following problem.

Referring to FIG. 13 (a), when resist of novolak-naphthoquinonediazide type 30 is applied as a thin layer on semiconductor substrate 2 having step 2a, the corner part 21 of step 2a is exposed for the lack of chemical affinity of semiconductor substrate 2 and resist of novalak-napthoquinonediziade type 30. In order to apply the resist of novolak-napthoquinonediziade type 30 so as to cover corner part 21, as shown in FIGS. 13 (b) and (c), the thickness of the resist becomes considerably large in the bottom part of step 2a. If, for example, step 2a is as thick as 0.7 μm, the resist of novalak-naphthoquinonediazide type 30 in the bottom part of step 2a attains a thickness of about 1.5 μm.

Figure 13A:
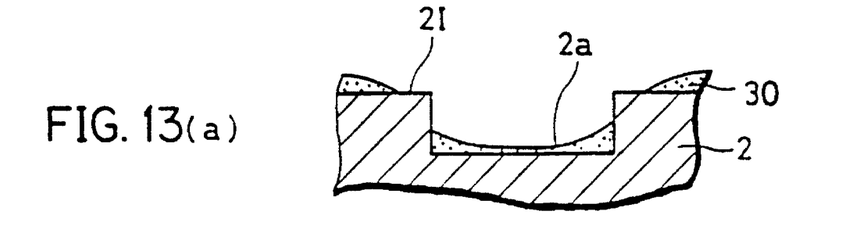
FIGS. 13(a)–(c) are a partially sectional view showing a semiconductor device in the steps of a manufacturing method of the semiconductor device in their order, including a method of forming a conventional antireflection film.
Figure 13B:
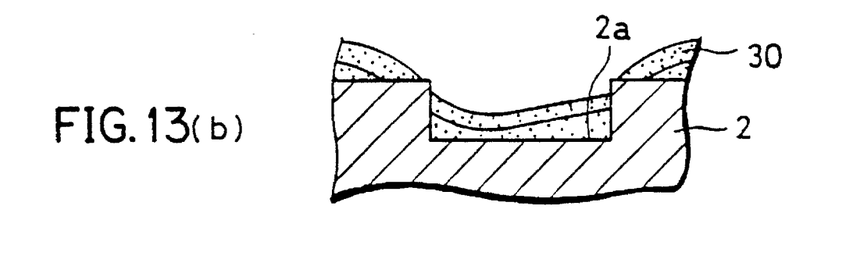
Figure 13C:
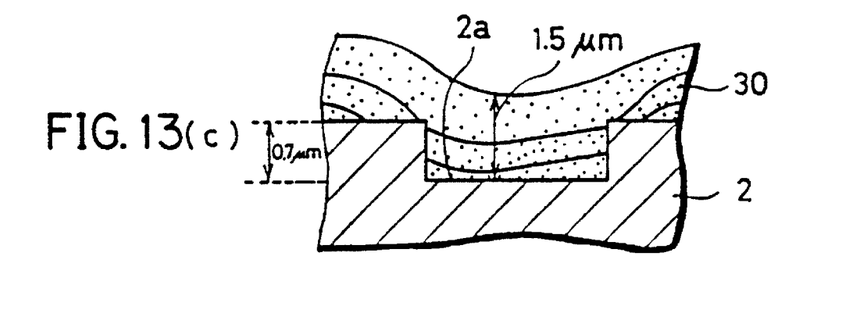
Figure 13D:
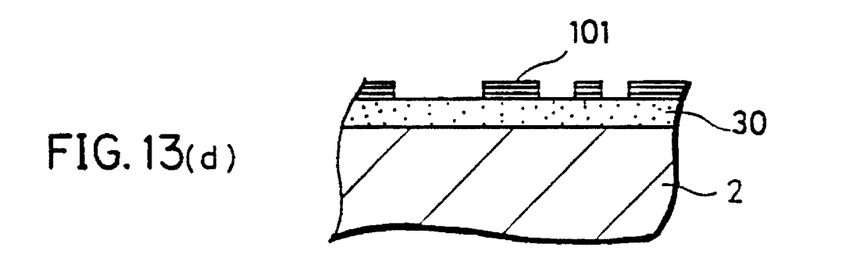
Figure 13E:
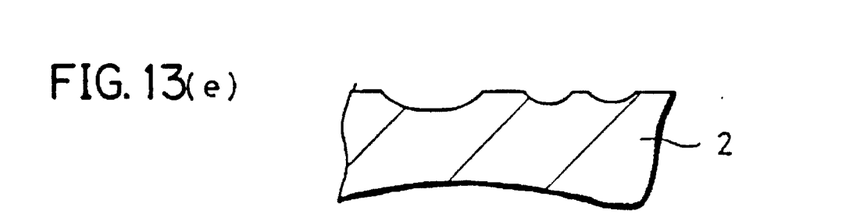

The antireflection film is completed by hard baking the resist of novalak-naphthoquinonediazide type 30 applied as thick as this. Thereafter, referring to FIG. 13 (d) resist for lithography 101 is applied onto antireflection film (30), and patterning is performed thereon. Then, using the patterned resist for lithography 101 as a mask, semiconductor substrate 2 and the antireflection film are etched at a time. At that time, there is almost no difference in the etching speeds of antireflection film 30 and resist for lithography 101. Referring to FIG. 13 (e), the size of semiconductor substrate 2 cannot be controlled successively in the process of etching the same.

SUMMARY OF THE INVENTION

It is therefore an object of the present invention to form a very small resist pattern by means of lithography using deep ultra violet light.

Another object of the present invention is to provide an improved method of forming a resist pattern by which a resist pattern is formed with its size successfully controlled and the size of an underlying substrate can be controlled successfully in the process of etching even when a step portion is on the semiconductor substrate.

Yet another object of the present invention is to provide an improved method of forming a resist pattern by which the change of the size of a resist pattern due to intra film multiple reflection effect can be restricted.

A still further object of the present invention is to provide an improved method of forming a resist pattern by which the change of the size of a resist pattern due to intra film multiple reflection effect can be restricted even when a conventional resist of chemical amplification negative type is used.

An additional object of the present invention is to provide an organic silane compound for forming an antireflection film suitable for the above-described methods.

A method in accordance with the present invention is a method for forming a resist pattern on a substrate by means of lithography using far-ultra violet light. An organic silane compound for forming an antireflection film is applied onto the surface of a substrate, contains a silicon atom, a leaving group bound to the silicon atom and replaceable with a hydroxyl group existing in the surface of the substrate for covalently binding the substrate and the organic silane compound, and a substituent group absorbing the far-ultra violet light. Resist is applied onto the surface on which the organic silane compound has been applied. Selective exposure is performed onto the resist using the far-ultra violet light. Then, the resist is subject to development.

An organic silane compound in accordance with another aspect of the present invention is for forming an antireflection film applied onto the substrate, prior to application of resist, in order to form a resist pattern on the substrate. The organic silane compound includes a silicon atom. Bound to the silicon atom is a leaving group replaceable with a hydroxyl group existing in the surface of the substrate for covalently binding the substrate and the organic silane compound. The substituent group absorbing the far-ultra violet light is bound to the silicon atom.

According to a method of forming a resist pattern in accordance with the present invention, an organic silane compound for forming an antireflection film is applied onto a surface, prior to application of resist to the substrate. Containing a substitute group absorbing far-ultra violet light, the organic silane compound functions excellently as an antireflection film, reducing the effect of intra film multiple reflection.

The organic silane compound has a leaving group replaceable with a hydroxyl group existing in a surface of the semiconductor substrate for covalently binding the substrate and the organic silane compound. Thus, the organic silane compound is strongly bound by covalence with the substrate as a result of reaction with the hydroxyl group existing in the surface. Therefore, even with a step portion in the surface of the substrate, the antireflection film can cover the surface of the substrate, the corner part of the step portion, the sidewall and the bottom of the recess of the step portion, without increasing the thickness of the film. The antireflection film obtained is thin and can therefore be removed readily at the time of etching the substrate.

The foregoing and other objects, features, aspects and advantages of the present invention will become more apparent from the following detailed description of the present invention when taken in conjunction with the accompanying drawings.

DETAILED DESCRIPTION OF THE PREFERRED EMBODIMENTS

Now, description will be provided on one embodiment of the present invention in conjunction with the drawings.

FIG. 1 is a partially sectional view showing a semiconductor device in the steps of a manufacturing method in accordance with the embodiment of the present invention in their order.

Figure 2A:
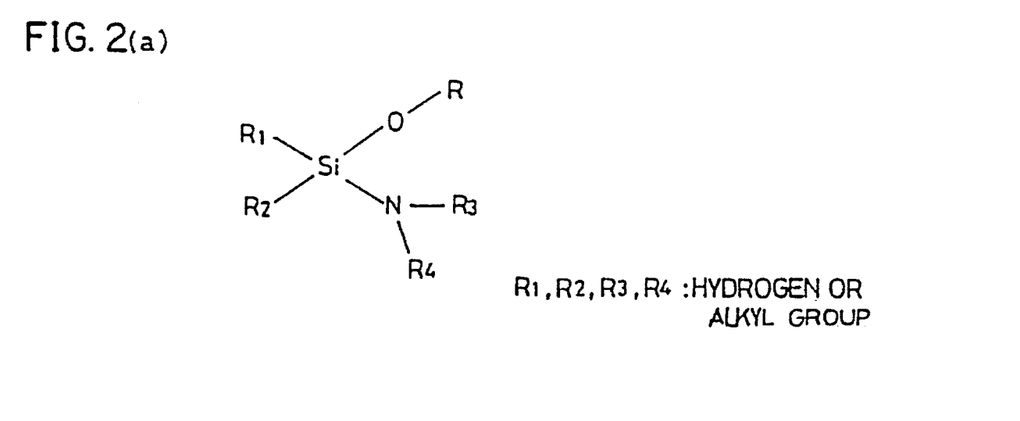
FIGS. 2(a)–(c) are is a representation showing the chemical structural formula of an organic silane compound used for the present invention and the reaction formula for manufacturing thereof.
Figure 2B:
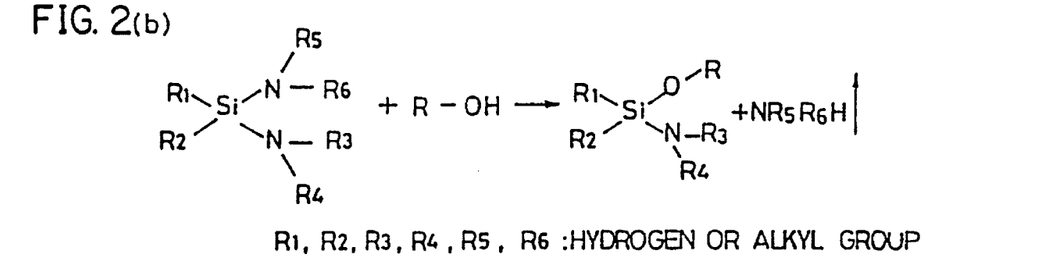
Figure 2C:
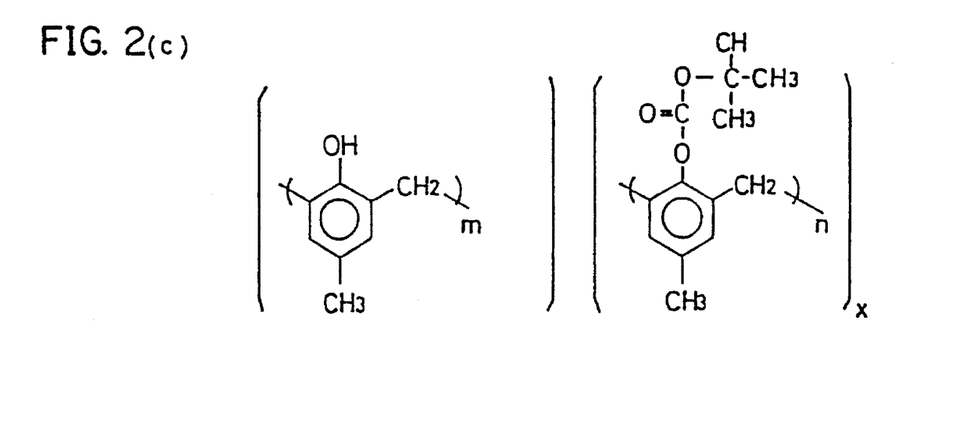

Referring to FIGS. 1 (a), an organic silane compound layer which functions as an antireflection film is formed on the surface of a silicon substrate 2 (the organic silane compound, as will be described later, has a function of closely contacting resist 3 and silicon substrate 2 and is therefore referred to as a contact reinforcing layer 1). Contact reinforcing layer 1 is formed by spin-coating silicon substrate 2 with an organic silane compound represented by the chemical structural formula shown in FIG. 2 (a). After the spin coating, silicon substrate 2 is baked at a temperature as high as about 90° C. In FIG. 2 (a), each of substituent groups $R_1$, $R_2$, $R_3$, $R_4$ is hydrogen or an alkyl group. The substituent group R is an organic molecule highly absorbent to far-ultra violet light such as excimer laser light. A nevolak resin shown in FIG. 2 (c), for example, is selected for the organic molecule absorbing far-ultra violet light. The organic silane compound shown in FIG. 2 (a) is, as shown in FIG. 2 (b), obtained by the condensation reaction with deamination of bis (dialkylamino) dialkylsilane and a novolak resin. The novolak resin is shown in FIG. 2 (c). The condensation reaction proceeds at an atmospheric temperature by mixing these components.

Although the substituent groups $R_1$, $R_2$, $R_3$, $R_4$, $R_5$, $R_6$ are not specified, the condensation reaction shown in FIG. 2 (b) proceeds smoothly when they are hydrogen methyl or ethyl groups. Especially, when $R_1$, $R_2$, $R_3$, $R_4$, $R_5$, $R_6$ are all methyl groups, bis (dimethylamino) dimethylsilane is preferably used.

Figure 1A:
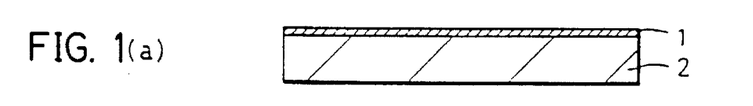
FIGS. 1(a)–(f) are a partially sectional view showing a semiconductor substrate in the steps in the order of a method of forming a resist pattern in accordance with one embodiment of the present invention.
Figure 1B:
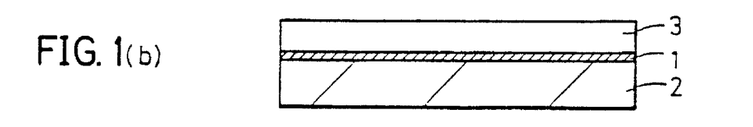
Figure 1C:
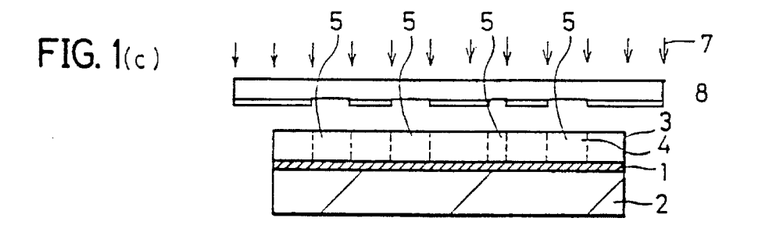
Figure 1D:
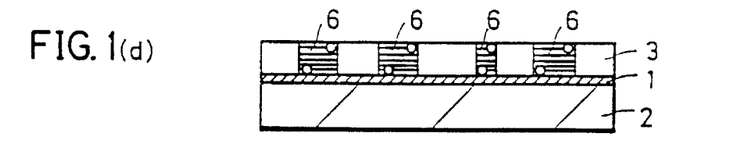
Figure 1E:
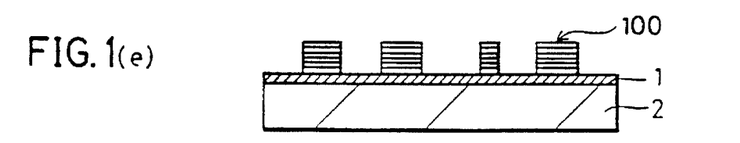
Figure 1F:
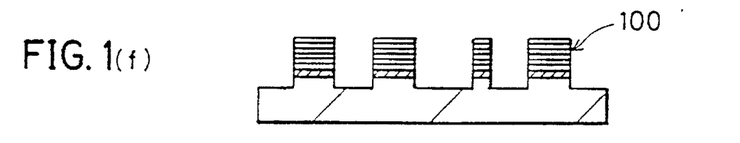

Referring to FIGS. 2 (c) and 1 (b), the affinity of contact reinforcing layers 1 and resist of chemical amplification negative types 3 subsequent to be applied is increased by capping a part of the hydroxyl groups of the novolak resin with a t-butyloxycarbonyl (t-BOC) group. The cap ratio is preferably in the range of about 0.3 to 0.7.

Figure 3A:
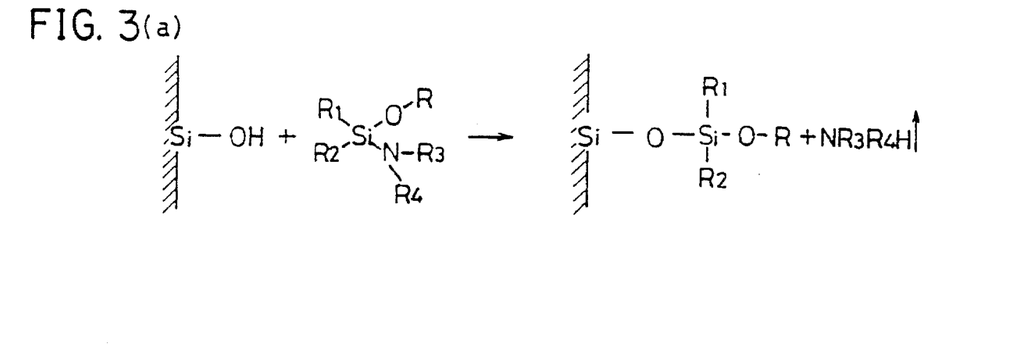
FIGS. 3(a)–(c) are is a representation showing the reaction of an organic silane compound used for the present invention and a hydroxyl group in the surface of a substrate.
Figure 3B:
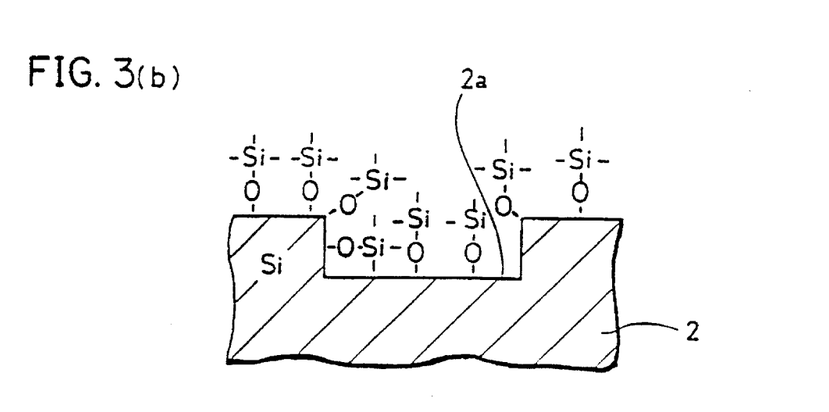
Figure 3C:
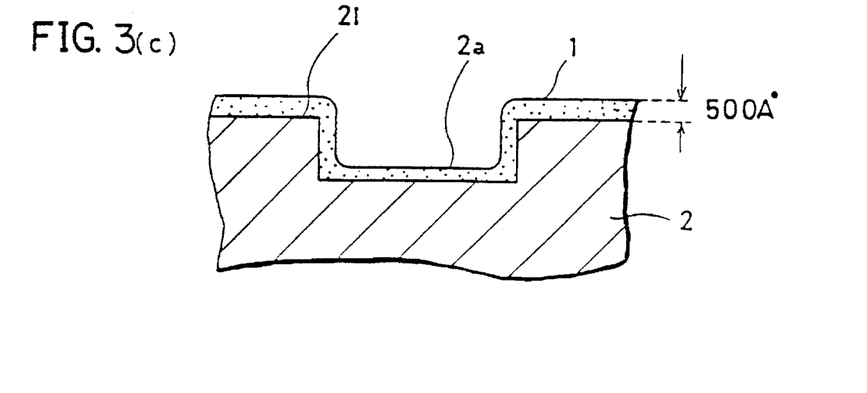

FIG. 3 is a representation showing the reaction which takes place in the surface of silicon substrate 2 when the organic silane compound is applied onto silicon substrate 2.

Referring to FIG. 3 (a), the organic silane compound is covalently bound to the surface of the silicon substrate by the condensation reaction with the deamination. The condensation reaction proceeds when a hydroxyl group attacks an Si atom and a leaving group, amine ($NR_3R_4H$) is removed. The condensation reaction proceeds rapidly at room temperature. The organic silane compound reacts with hydroxyl groups existing in the surface of silicon substrate 2, and the side walls and bottom of stepped portions 2a by simply being applied to silicon substrate 2. Consequently, referring to FIG. 3 (c), even with step portions 2a existing in the surface of silicon substrate 2, the surface of silicon substrate 2, the corner parts 21 of the stepped portion, and the sidewalls and bottom surfaces of the recess of step portion 2a can be covered with contact reinforcing layer 1 which functions as an antireflection film without increasing the film thickness. The film thickness of the resultant contact reinforcing film is about 500Å.

Referring back to FIG. 1 (b), contact reinforcing layer 1 was spin-coated with resist layer of chemical amplification negative type having a thickness in the range from 1.0 to 1.5 μm, and then soft-baking was performed thereto at a temperature in the range from 90° to 130° C. A conventional resist of chemical amplification negative type as shown in FIG. 6 was used. Referring to FIG. 1 (c), far-ultra violet light such as excimer laser light 7 was selectively irradiated upon resist layer of chemical amplification negative type 3 through reticle 8. Proton acid 4 is produced in the exposed part 5 of resist layer of chemical amplification negative type 3 by the selective irradiation of excimer laser light 7. The proton acid 4, as shown in FIG. 9, advances the cross linking reaction of resins. Contact reinforcing layer 1 functions as antireflection film, and, therefore, the effect of intra resist film multiple reflection in the exposed part 5 is tremendously reduced.

Referring to FIG. 1 (d), the resist is baked for about 1 to 2 minutes at a temperature in the range from 110° to 130° C. after the exposure. The cross linking reaction of base resins as shown in FIG. 9 proceeds in the exposed part 5 of the resist 3 by the baking. The crosslinking part 6 has a reduced solubility into an alkaline developing agent.

Referring to FIG. 1 (e), when developed with an alkaline developing agent of a suitable concentration, the non-exposed part of resist film 3 dissolves into the alkaline developing agent, and a resist pattern of negative type 100 is formed.

Referring to FIG. 1 (f), using resist pattern 100 as a mask, silicon substrate 2 and contact reinforcing layer 1 are etched at a time. At that time, having a small film thickness, contact reinforcing layer 1 is readily etched away. Consequently, the size of silicon substrate 2 can be controlled as etching proceeds.

Figure 4:
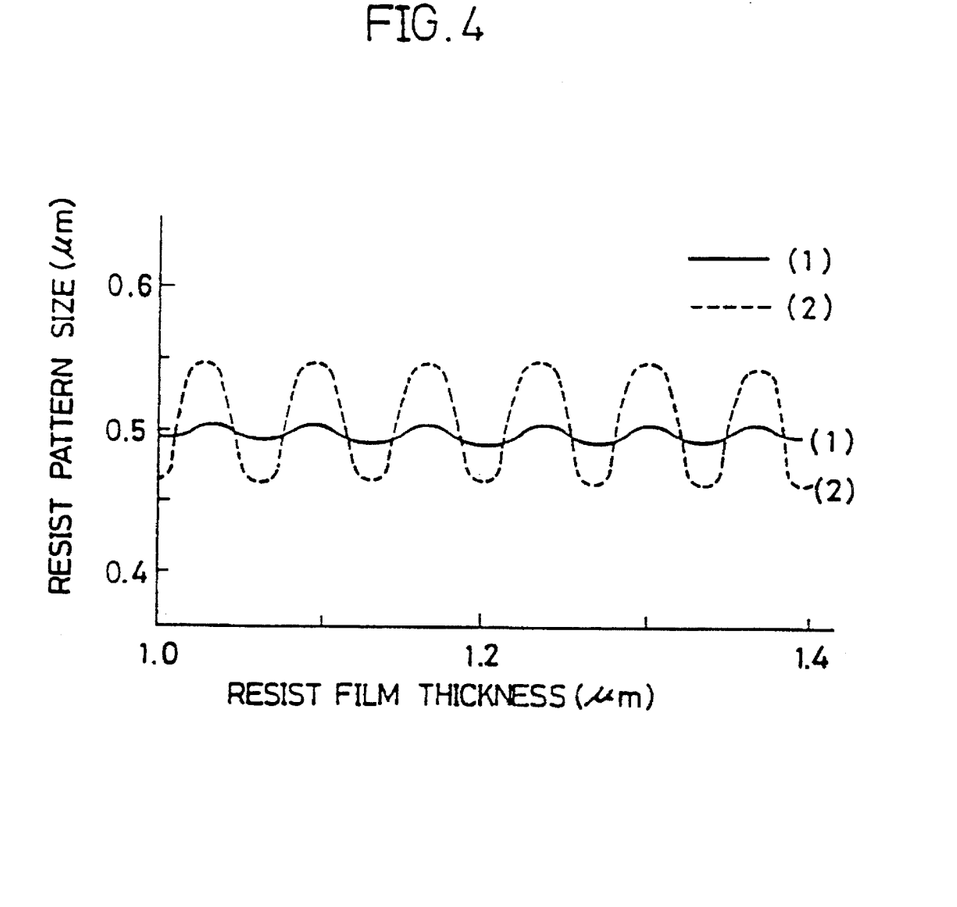
FIG. 4 is a representation showing a reduction in the effect of intra film multiple reflection effect for illustrating the effect of the present invention.

FIG. 4 is a representation showing the dependence of resist pattern size on resist film thickness. In FIG. 4, curve (1) represents data when the organic silane compound was used for the contact reinforcing layer, and curve (2) represents data when the organic silane compound was not applied. It was proved that treating the surface of the substrate with the organic silane compound prior to application of resist tremendously restricts the effect of intra-film multi-reflection.

In the above-described embodiments, a p-cresol novolak resin having part of the hydroxyl groups capped with t-BOC groups was used as an organic substance having high absorption to a far-ultra violet light such as an excimer laser. However, the present invention is not limited thereto and similar effects to the above-described embodiments can be employed if other organic polymers containing aromatic ring highly absorbable in a far-ultra violet light region and having a hydroxyl group, or organic coloring matters are used. A coumarin derivative, a curcumin, etc. may be preferably used.

Figure 5:
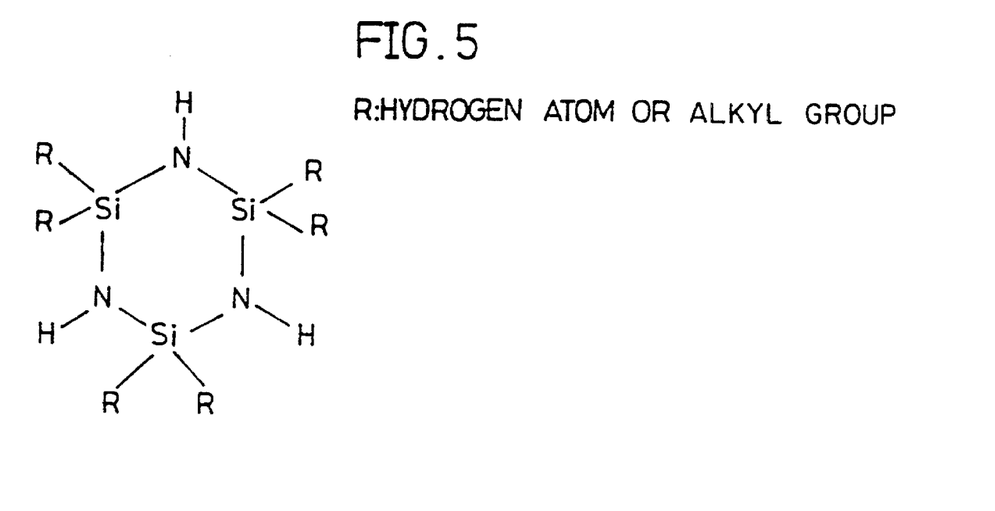
FIG. 5 is the chemical structural formula of another example of an organic silane compound used for the present invention.

Also, in the above-described embodiments, the cases have been illustrated in which bis (dialkylamino)dialkylsilane was used as an aminosilane compound containing at least two aminosilane groups as shown in FIG. 2 (b) which is a raw material for an organic aminosilane compound, but the present invention is by no means limited thereto, and hexaalkylcyclotrisilazane as shown in FIG. 5 may be used.

As described above, according to a method of forming a resist pattern in accordance with the present invention, an organic silane compound for forming an antireflection film is applied onto a substrate, prior to application of resist thereon. Having a substituent group absorbing far-ultra violet light, the organic silane compound functions excellently as an antireflection film, thereby reducing the effect of intra film multiple reflection.

Also, the organic silane compound contains a leaving group replaceable with a hydroxyl group existing in the surface of the substrate in order to bind the substrate and organic silane compound. Therefore, when applied onto the surface, the organic silane compound quickly reacts with the hydroxyl group in the substrate and is thereby bound with the substrate firmly. Accordingly, even with step portions existing in the surface of the substrate, the surface of the substrate, the corner part of the step portion, the sidewall and bottom surfaces of the recess of the step portion can be covered in an even manner with an antireflection film without increasing the thickness of the film. The anti reflection film is thin and can therefore be readily removed at the time of etching the substrate. The size of a resist pattern can therefore be controlled successfully even with the step portion on the substrate, and the size of the underlying substrate can be controlled successfully as etching proceeds.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A method of forming a resist pattern on a substrate by lithography using deep ultraviolet light, comprising the steps of:

providing an organic silane compound for forming an antireflection film in the surface of said substrate, the organic silane compound being of the formula where $R_1$, $R_2$, $R_3$ and $R_4$ individually represent hydrogen or an alkyl group, and R represents a substituent group absorbing deep ultraviolet light;

coating said substrate with said organic silane compound;

applying resist onto said substrate coated with said organic silane compound;

exposing selectively said resist using deep ultraviolet light; and developing said resist.

2. A method as recited in claim 1, wherein $R_1$, $R_2$, $R_3$ and $R_4$ individually are hydrogen, methyl or ethyl groups.

3. A method as recited in claim 1, wherein said R includes a novolak resin.

4. A method as recited in claim 3, wherein 30 to 70% of the hydroxyl groups of said novolak resin are capped with a t-butyloxycarbonyl group.

5. A method as recited in claim 1, wherein said substituent group R includes an organic coloring matter.

6. A method as recited in claim 5, wherein said organic coloring matter is formed from coumarin.

7. A method as recited in claim 5, wherein said organic coloring matter includes curcumin.

8. A method as recited in claim 1, wherein said substrate includes a silicon semiconductor substrate.

9. A method as recited in claim 1, wherein said deep ultraviolet light includes excimer laser light.

10. A method as recited in claim 1, wherein said resist includes a chemical amplification negative resist.

* * * * *